United States Patent [19]

Stettner

[11] Patent Number: 5,140,162
[45] Date of Patent: Aug. 18, 1992

[54] SOLID-STATE PORT DIGITAL IMAGER

[76] Inventor: Roger Stettner, 2441 Foothill La., Santa Barbara, Calif. 93105

[21] Appl. No.: 506,948

[22] Filed: Apr. 9, 1990

Related U.S. Application Data

[63] Continuation-in-part of Ser. No. 325,137, Mar. 17, 1989.

[51] Int. Cl.⁵ .......................................... H01L 27/146
[52] U.S. Cl. ......................... 250/370.09; 250/370.11; 357/30
[58] Field of Search .................... 250/370.11, 370.09; 357/30 H, 30 G

[56] References Cited

U.S. PATENT DOCUMENTS

| | | | |
|---|---|---|---|
| 4,471,378 | 9/1984 | Ng | 358/110 |
| 4,695,716 | 9/1987 | Tandon et al. | 250/211 R |
| 4,700,076 | 10/1987 | Dorman et al. | 250/370.09 |
| 4,905,265 | 2/1990 | Cox et al. | 378/99 |
| 4,945,243 | 7/1990 | Arques | 250/367 |

FOREIGN PATENT DOCUMENTS

3836835  6/1989  Fed. Rep. of Germany ................ 250/370.11

Primary Examiner—Constantine Hannaher
Attorney, Agent, or Firm—Gottlieb, Rackman & Reisman

[57] ABSTRACT

A high resolution high-energy x-ray digital imager suitable for patient x-ray diagnosis and the location of bony landmarks in high energy radiation therapy. The imager employs an array of sensor chips which need not lie in a plane in order to provide overlap of non-active components and direct readout (non - CCD) signal processing electronics incorporating a switched capacitor per detector readout to sense a short x-ray pulse. The switching prevents dark current from discharging sensing capacitors and corrupting the data signal.

25 Claims, 11 Drawing Sheets

SOLID-STATE PORT DIGITAL IMAGER

BACKGROUND OF THE INVENTION

This application is a continuation-in-part of application Ser. No. 325,137, entitled High Resolution Position Sensitive Detector, filed Mar. 17, 1989.

This invention relates to apparatus and methods employing focal plane array technology for x-ray diagnosis and for the identification of bony landmarks and therefore patient position prior to high energy radiation therapy. More specifically, this invention relates to a high-resolution, high-sensitivity, high-energy-x-ray sensor employing a solid state focal plane array with a novel detector and readout configuration.

There is a current need to verify patient position with respect to the radiation field of accelerators employed in the radiation treatment of cancerous tumors. Studies indicate that film images of the radiation field with respect to the patient (port images), taken prior to radiation therapy, at low dose with the therapy accelerator, reduce positioning errors. Reduction of positioning errors is highly desirable because it increases the effectiveness of the therapy in destroying the cancer at tumor margins and prevents damage to healthy organs outside the tumor margins. Because of the time required to produce, develop and interpret film images they are not often used in the therapy procedure.

A difficulty in interpreting the film images results from the fact that the therapy x-rays are high-energy and are not absorbed by bone as well as lower energy diagnostic x-rays. The resulting film images are of low contrast. More easily interpretable images can be produced using higher contrast film in conjunction with image digitalization technology and computational image processing, but there is a trade-off between sensitivity and resolution. Even with state of the art digitizing image technologies there is not adequate resolution (say 0.1 cm) for optimal patient positioning.

Film substitutes (fluorescent screen, scintillator and ionization chamber technologies), used in conjunction with image digitization technology, can avoid the time delay required for film processing and potentially can be used on line, in real time. But, because of the low-radiation sensitivity of these detector technologies, and the inefficiency of converting the x-rays to a digital image, the image radiation doses required for high-contrast are a substantial fraction of the doses required for the therapy itself. Consequently, the benefits derived from pre-therapy position-verification imaging are not practically achievable, in real time with current technology.

A digitized, on line, real time image is also highly desirable in diagnostic radiology. (Diagnostic radiology x-rays are about a factor of ten lower in energy than therapy high-energy-x-rays.) A digitized image can be processed to enhance local contrast, revealing certain pathology more clearly than ordinary x-ray films. With the proper x-ray converter screen, e.g. a rare earth scintillator, the present invention provides enhanced imaging even at these lower energies.

OBJECT OF THE PRESENT INVENTION

It is an object of the present invention to provide a high-resolution, high-efficiency, direct digitization, high-energy-x-ray sensor array employing a solid state focal plane array having an improved detector and readout configuration.

It is a further object of the present invention to provide a sensitive, high-resolution, real time processing, digitizing imager for patient placement verification prior to high energy radiation therapy.

It is a still further object of the present invention to provide a high-resolution, high-efficiency, direct digitization, diagnostic x-ray sensor array as a component of a diagnostic x-ray imager.

DESCRIPTION OF A PREFERRED EMBODIMENT OF THE INVENTION

Figure 1:
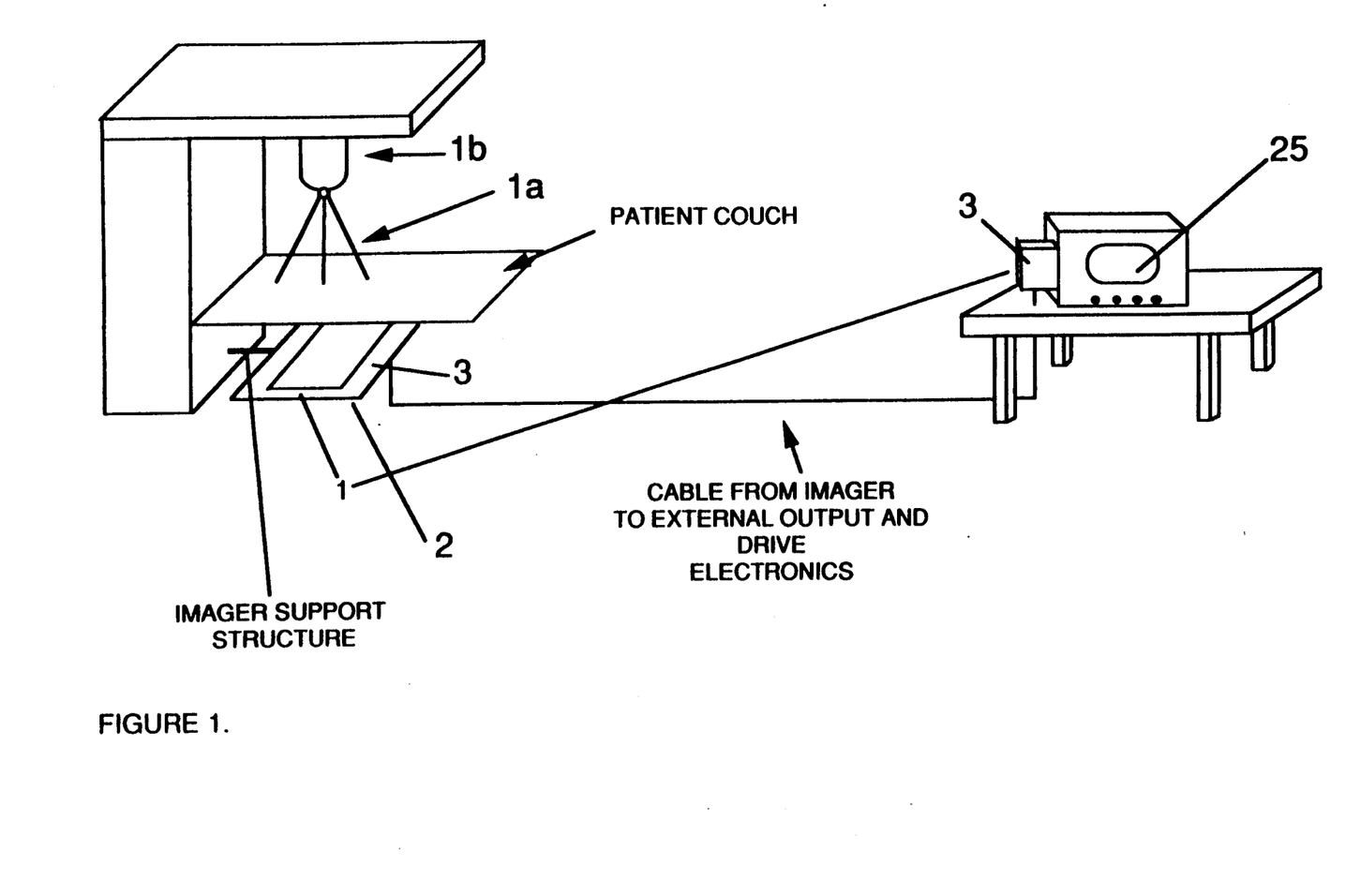
FIG. 1 is a perspective view of the preferred embodiment of the Solid-State Port Digital Imager of the present invention in position to image a patient.

A preferred embodiment of the present invention, designed to sense and digitize data obtained from the passage of high-energy diagnostic or x-rays through bony landmarks is depicted in FIG. 1. The x-rays (1a) may be Bremsstrahlung generated by an electron beam of about 4–6 Mev (million electron volts) within the therapy accelerator (1b). The overall device 1 is preferably a sensitive, high-resolution port x-ray imager, having a sensor array 2 positioned to receive x-rays that penetrate the patient, and external electronics 3. Alternatively, the x-rays may be diagnostic x-rays.

Figure 2A:
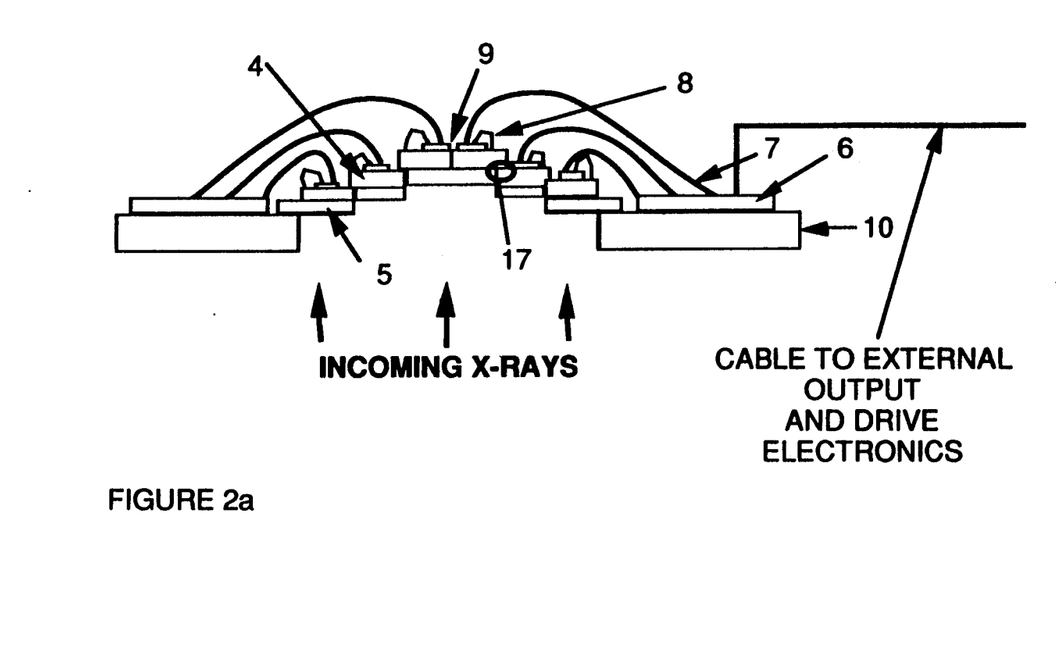
FIG. 2a is a detailed cross-section of the sensor array of the present invention.
Figure 2B:
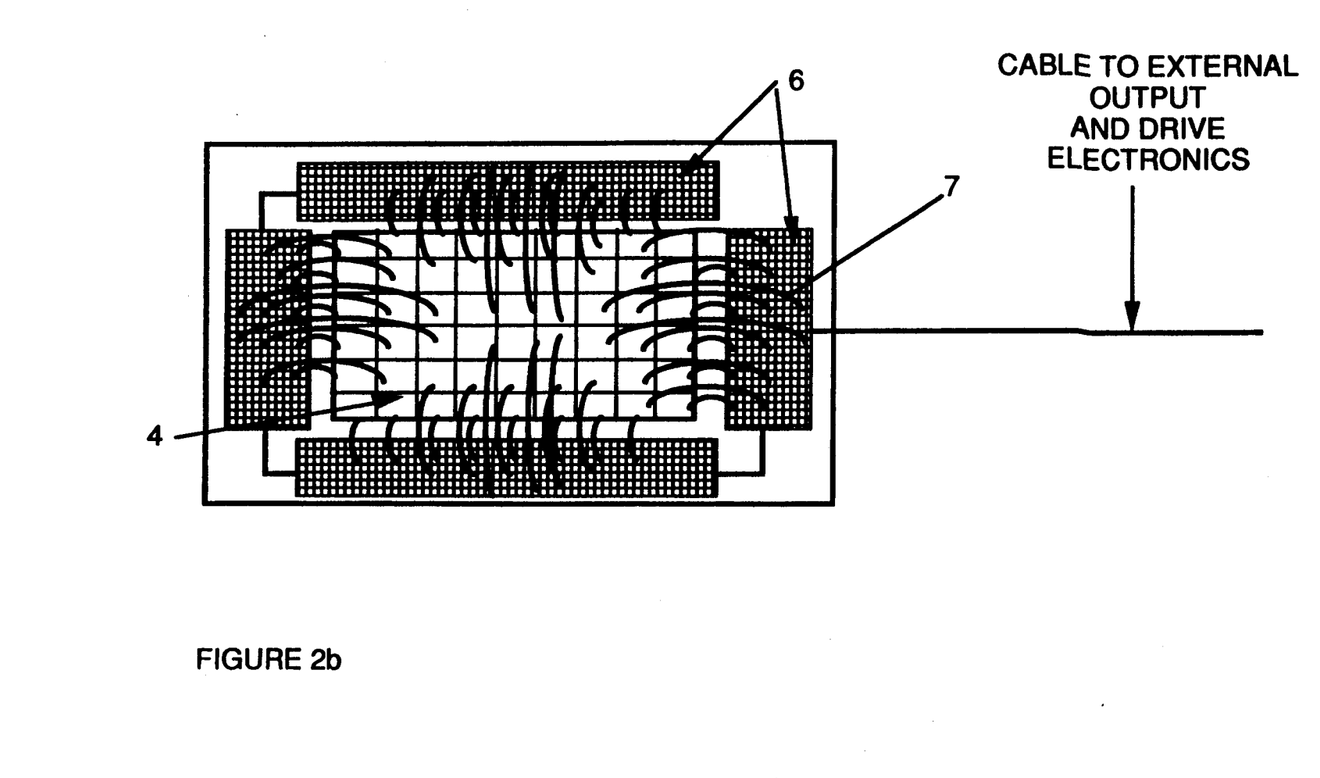
FIG. 2b is a detailed top view of the sensor array of the present invention.

FIGS. 2a and 2b show in more detail the sensor array 2 of the present invention. The entire array is roughly 17 inches by 24 inches. As shown in the top view, the sensor array is a rectangular matrix of abutting imager structure components sensor chip arrays (SCAs) 4, which need not lie in a plane (in order to provide overlap of non-active components as explained below) together with tungsten (or other high-density metal) converters 5 underlying each SCA and array signal processing electronics 6, around the periphery of the array. A novel feature of the imager is on the array positioning of the array signal processing electronics 6, a portion of the output electronics (refer to FIG. 9). SCA drive capacity is low and on array positioning of the amplifier and digitizer allows detector signals to be driven off the array, for further processing, without reduction in the signal to noise ratio.

In the case of the diagnostic imager the tungsten converter is replaced by rare earth or other scintillator material 5, conventionally used as screens in diagnostic imaging. The PIN detector 11 is sensitive to the visible light photons from the scintillator material.

In either case, cables 7 lead off each SCA 4 to the array electronics 6. Wire bonds 8, connect the SCA to a small circuit board 9 which is connected to the cable 7. High-density x-ray shielding 10 supports the imager structures and shields the array signal processing electronics 6 from the x-rays, whose direction is shown in the figure.

Figure 3:
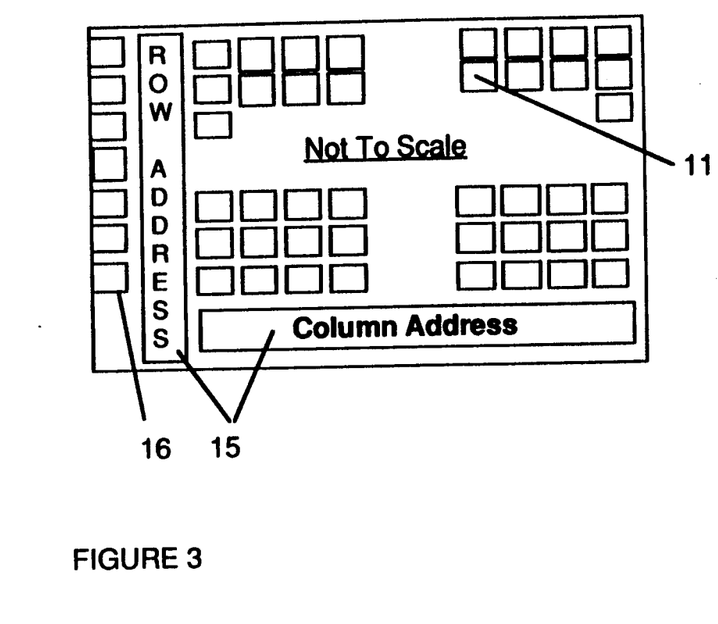
FIG. 3 is a top view of the Sensor Chip Array of the present invention.

An individual sensor chip array (SCA) 4 is shown in greater detail in FIG. 3. It is 6×6 cm in size, for the high-energy-x-ray imager. For the diagnostic x-ray imager the SCA's could be as small as 1×1 cm in size. The SCA comprises a N×M rectangular array of square PIN detectors 11. Such a PIN detector is a P-N junction diode with an intrinsic silicon layer, the I layer sandwiched between. The active detector layer is the intrinsic region. For the high-energy-x-ray imager each detector is 900µ on a side and separated by 100µ from its neighbors.

For the diagnostic x-ray imager each detector will be from 25µ to 200µ on a side and separated by 5µ to 40° from its neighbors.

Figure 4:
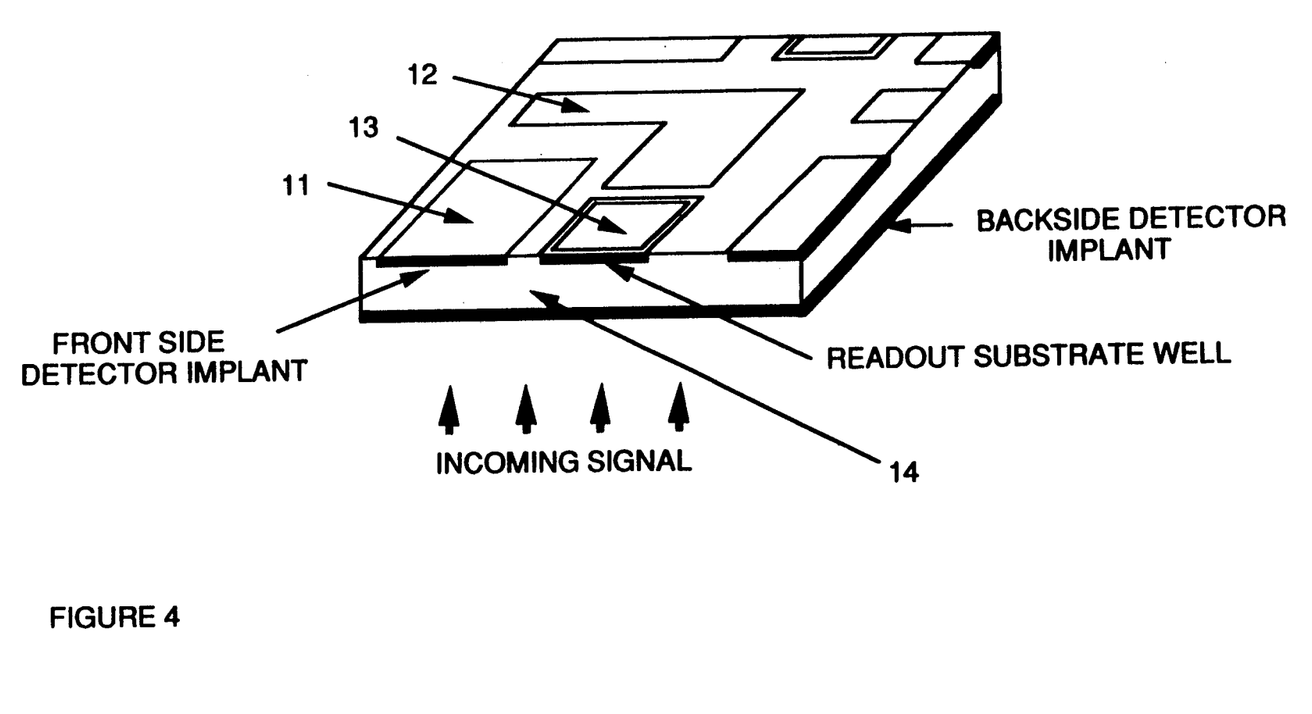
FIG. 4 is a detailed perspective view of a unit cell comprising a detector, capacitor and associated readout electronics of the present invention.

FIG. 4 shows in greater detail, the configuration of each individual unit cell of a sensory chip array. Associated with each PIN detector 11, as shown in FIG. 4, is a sense capacitor 12 (for collecting the charge generated in the detector 11) and readout electronics 13 for controlling the resetting and reading out of the sense capacitor 12 voltages. The detector, associated capacitor and associated readout electronics is called the unit cell, and resides on an intrinsic (i.e., lightly N-doped) silicon substrate 14.

For the high-energy-x-ray imager, each sensor chip array is configured as a N×M array of unit cells (a nommal value is 60×60), each comprising a square detector 900 microns on a side. The ultimate resolution of the instrument is determined by the lateral detector dimension. Resolutions higher than 0.1 cm is achieved by decreasing the unit cell detector size and increasing the number of unit cells in the array. The active detector volume is determined by the thickness of the Intrinsic Silicon Substrate 14 in FIG. 4 (nominally 0.05–0.1 cm) and the lateral detector dimensions. It is in this volume that Compton electrons create ionization and in which some of the x-rays are converted to Compton electrons.

In use, some of the high-energy-x-rays that pass through the patient produce Compton electrons in the high-density converter 5, shown in FIG. 2a. Other high-energy-x-rays that pass through the high-density converter 5 are converted to Compton electrons in the SCA detectors. The Compton electrons ionize atoms in the PIN detectors and the resulting charge is collected on the sense capacitors (12, see FIG. 4) as a voltage. These voltages are read off the SCA by means of the wire bonds 8, the small circuit board 9, and cable 7. The voltages are then amplified and digitized by the array signal processing electronics 6. The high-density metal converter 5 is from 0.02 cm to 0.1 cm thick and also serves as a support structure for the SCAs 4, as well as a shield for the Compton electrons generated in the patient's tissues.

On two sides of the sensor chip, as shown in FIG. 3, row and column address electronics 15 is positioned.

The function of this electronics is to permit selection of one of the nominal 3600 detectors addressed by an external 8 digit binary code. The chip space taken up by the row and column address wire bond pads 16 in FIG. 3 is not active for x-ray detection and the requirement for a continuously active array is satisfied by a one side chip overlap 17 as in FIG. 2.

For the high-energy-x-ray imager, a 0.1 cm contrast resolution is possible when identifying the boundary of 0.6 cm of bone in 20 cm of soft tissue using a therapeutic x-ray dose of 0.4 rads (unit of absorbed radiation energy per gram); with a dose of 0.1 rads of 0.2 cm resolution is possible.

Figure 5:
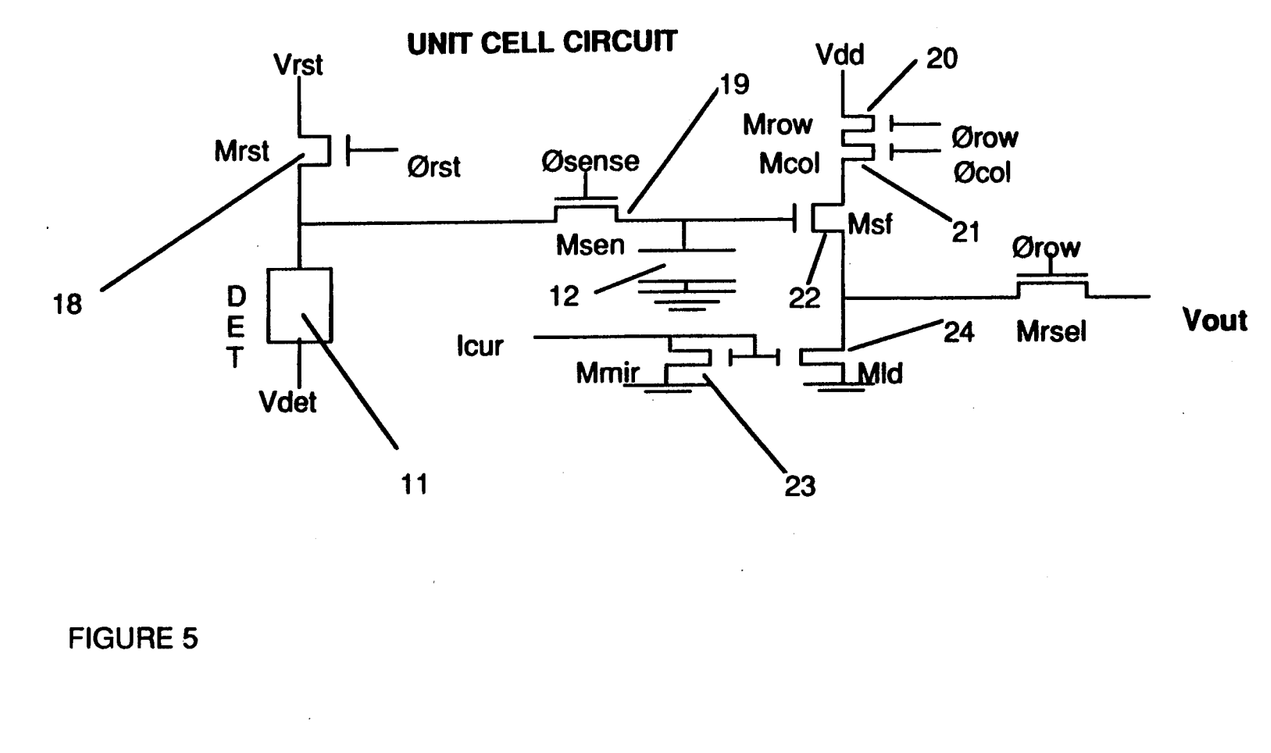
FIG. 5 is a schematic rendering of the readout electronics of the present invention.

The readout circuit, shown in FIG. 5, delivers the detector signal to the off-chip processing electronics and keeps the signal to noise ratio as high as possible. The readout circuit employs the direct readout approach (NON-CCD) which incorporates a switched capacitor per detector readout and multiplexer circuitry. This circuit represents a new and innovative design approach to sensing a short detector pulse from a therapy x-ray source in a radiation environment. Radiation hardening techniques known to persons skilled in this art are preferably implemented in the design of the readout. This includes thin gate oxides, thin oxide from channel stop to MOSFET'S and a enhanced grounding scheme per unit cell. Fortunately, MOSFET radiation effects are minimized at room temperature (~300K) which is the imager operating temperature. The readout electronics is expected to be hard to $10^6$–$10^7$ rads with MOSFET technology, and $10^8$ rads with either a MOSFET trapped charge neutralization procedure of JFET technology.

During the circuit operation/data cycle, the reset MOSFET (Mrst) 18 and the sense MOSFET (Msen) 19 are initially both on resetting the PIN detector and the sense capacitor (Csen) 12 to a set voltage (Vrst.).

Figure 6:
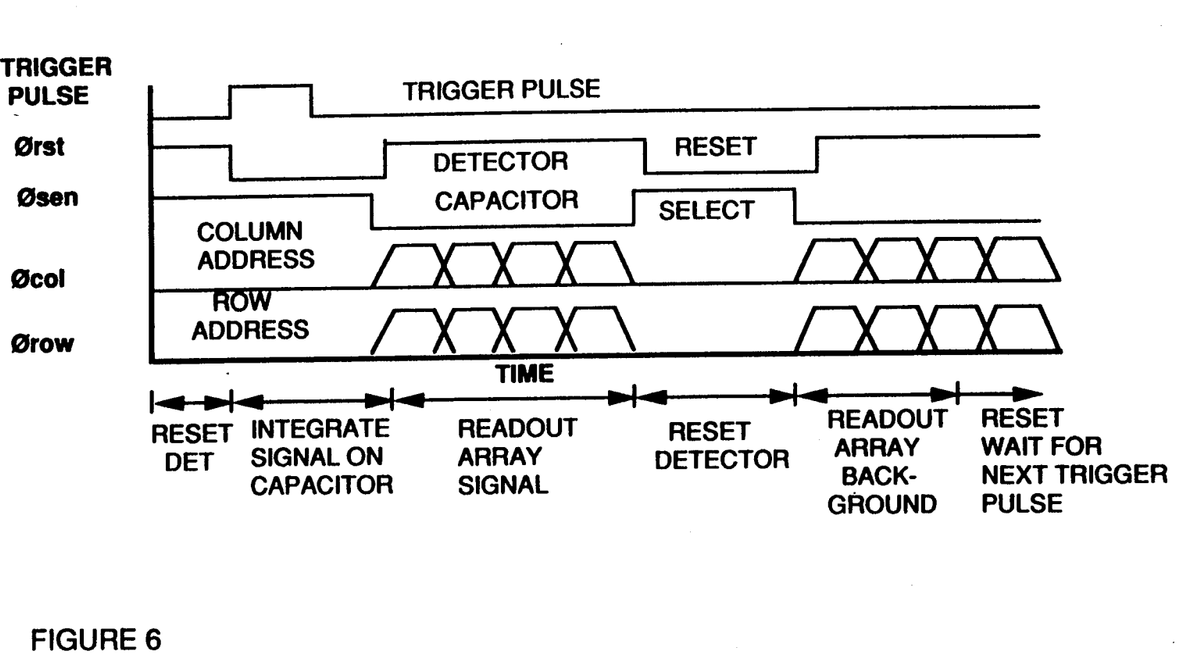
FIG. 6 is a timing chart for the electronics of the present invention.

The data cycle timing diagram appears in FIG. 6. The trigger pulse from the diagnostic or therapy x-ray source initiates the start of a data cycle. Detector reset ($\phi$rst) is then turned off for all detectors allowing detector current to be integrated on the sense capacitor (Csen) 12. A short time after the trigger pulse, the x-ray source exposes the sensor array (2, FIGS. 1 and 2) to x-rays. Therapy x-ray photons are converted to Compton electrons in the converter (FIG. 2, 5) mounted to the backside of the SCA and also converted in the PIN 11 detector material. Diagnostic x-rays are converted to "visible" light photons in the scintillator 5, and the "visible" light photons are converted to electron-hole pairs in the PIN 11 detector material.

Electron-hole pairs generated in the PIN 11 are swept out of the detector by its internal electric field and delivered to the sense capacitor 12. A short time after the x-ray source is off, the sense MOSFET (Msen) 19 is turned off for all unit cells. This action will prevent detector dark current from discharging the sense capacitor 12 and destroying or corrupting the data signal. The transistor switch (Msen 19, FIG. 5) isolates the detector from the readout circuitry. The detector is switched into the readout circuit when the x-ray pulse is on and out of the readout circuit when the x-ray pulse is off. This operation reduces the detector dark-current noise, increasing the signal to noise ratio and therefore increasing the image quality. This action also allows for a slower data rate coming off the SCA which lessens the complexity of both the readout and supporting sensor electronics. The address decoder (15, FIG. 3) cycles through all N×M combinations where each combination enables MOSFET'S (Mrow) 20 and (Mcol) 21 in each unit cell. This enabling allows MOSFET (Msf) 22 to sense the charge on the sense capacitor (Csen) 12 and generate an appropriate source follower voltage (Vout). The load for this source follower is generated by the combination of MOSFET'S (Mmir) 23 and (Mld) 24. This pair of MOSFET'S forms a current mirror. The current in line (Icur) will be mirrored in MOSFET (Mld) 24. Current mirror loads always show excellent uniformity and the current in MOSFET (Mld) 24 is always known.

The source follower per unit cell approach is used to drive the selected row and column output line in view of the parasitic capacitance from the row and column line. Power dissipation per SCA is kept to a minimum due to the fact that only one unit cell is selected at any given time.

The operating cycle described above is repeated with the x-ray source turned off. This second data cycle is a background reference signal that will be subtracted from the first cycle. In this way better SCA sensitivity and uniformity can be achieved. This technique has the advantage of subtracting out any anomalous radiation effects induced by the x-ray source.

Figure 7:
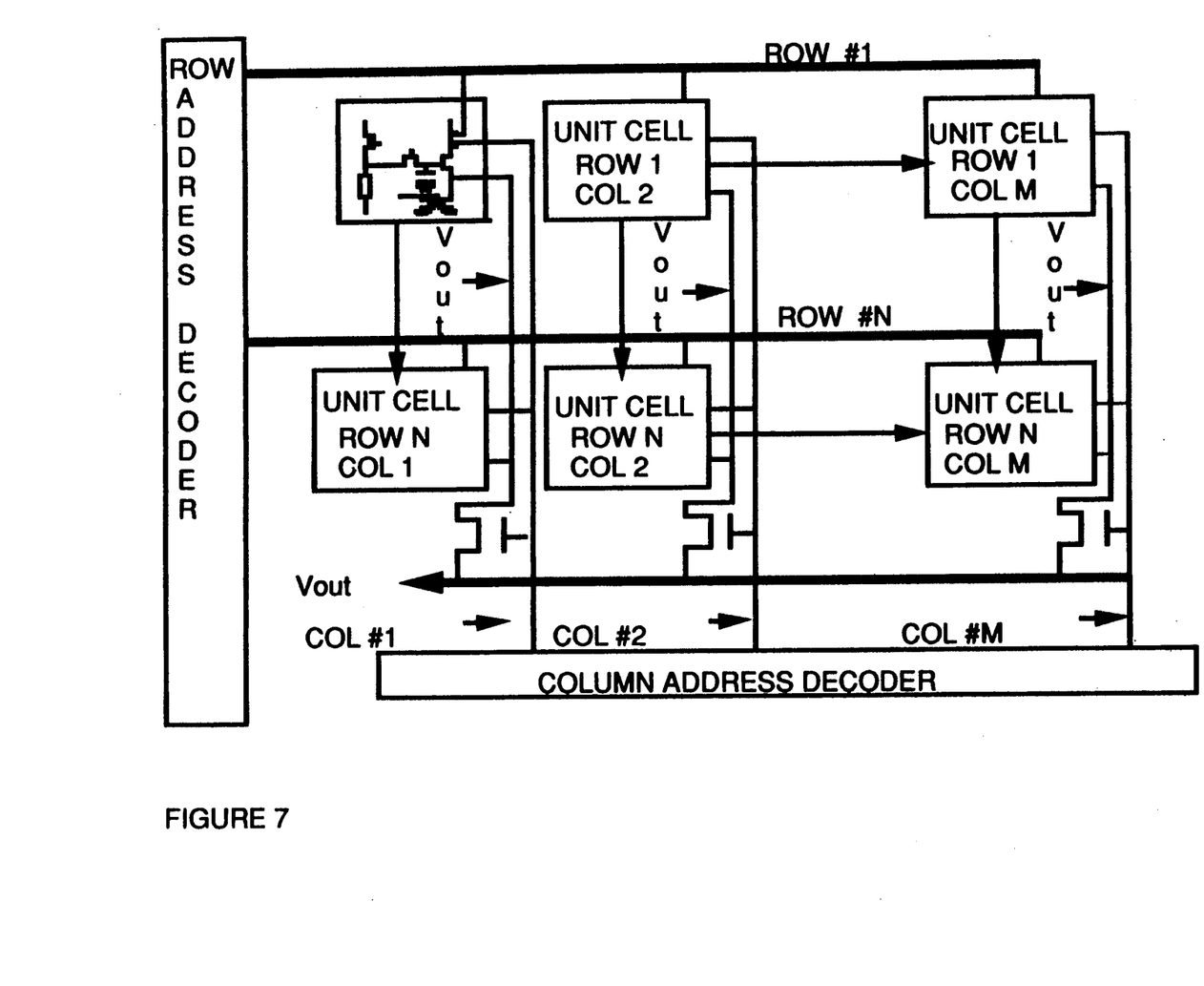
FIG. 7 is a schematic of the functioning of the on-chip address decoder of the present invention.

The address decoder is shown in FIG. 7. It assures a unique output signal for each and every detector element in a timely manner. A unique aspect of this decoder is the fact that the unit cell readout has to drive only one row and one column. This is of particular importance because of the limited drive capability of each unit cell readout.

Figure 8:
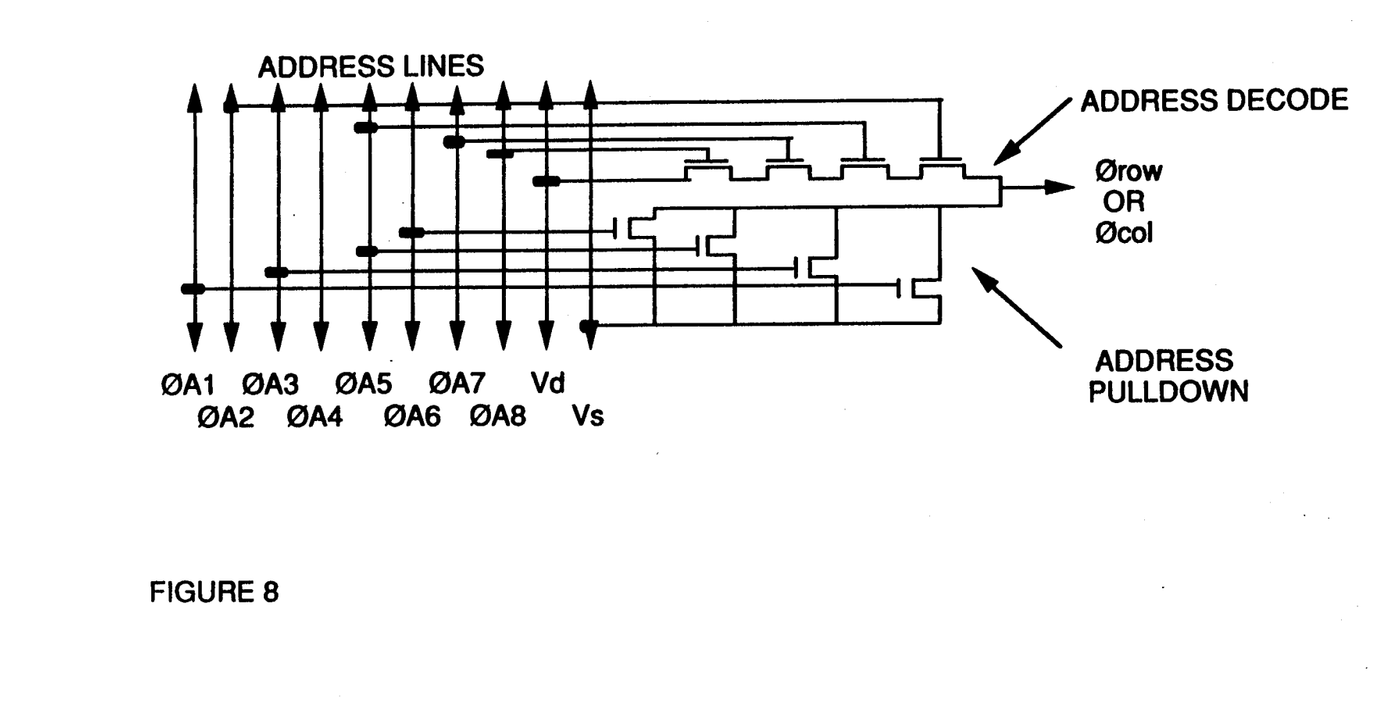
FIG. 8 is a schematic rendering of the circuitry of the address decoders of the present invention.

The row/column address decoder circuit is shown in FIG. 8. This circuit is an 8 choose 4 decoder requiring 8 address lines to select 60 combinations. (The specific decoder depends upon the N×M SCA, 60 combinations is a nominal value). The decoder is of proven design with a high process yield and low failure rate. Four address MOSFET'S select the desired row/column through the use of eight address lines: four transistors must be turned on to select a row (or column); eight lines from the external electronics perform this function. The address pulldown MOSFET'S select the previously addressed row/column line and make it inactive by pulling it to a logical zero.

The sensor electronics features low risk concepts coupled with mature technology to meet all Digital Imaging signal processing requirements. The electronic sub-system is partitioned into two functional units. The Output Electronics (OE) and the Drive Electronics (DE) make-up these two units.

Figure 9:
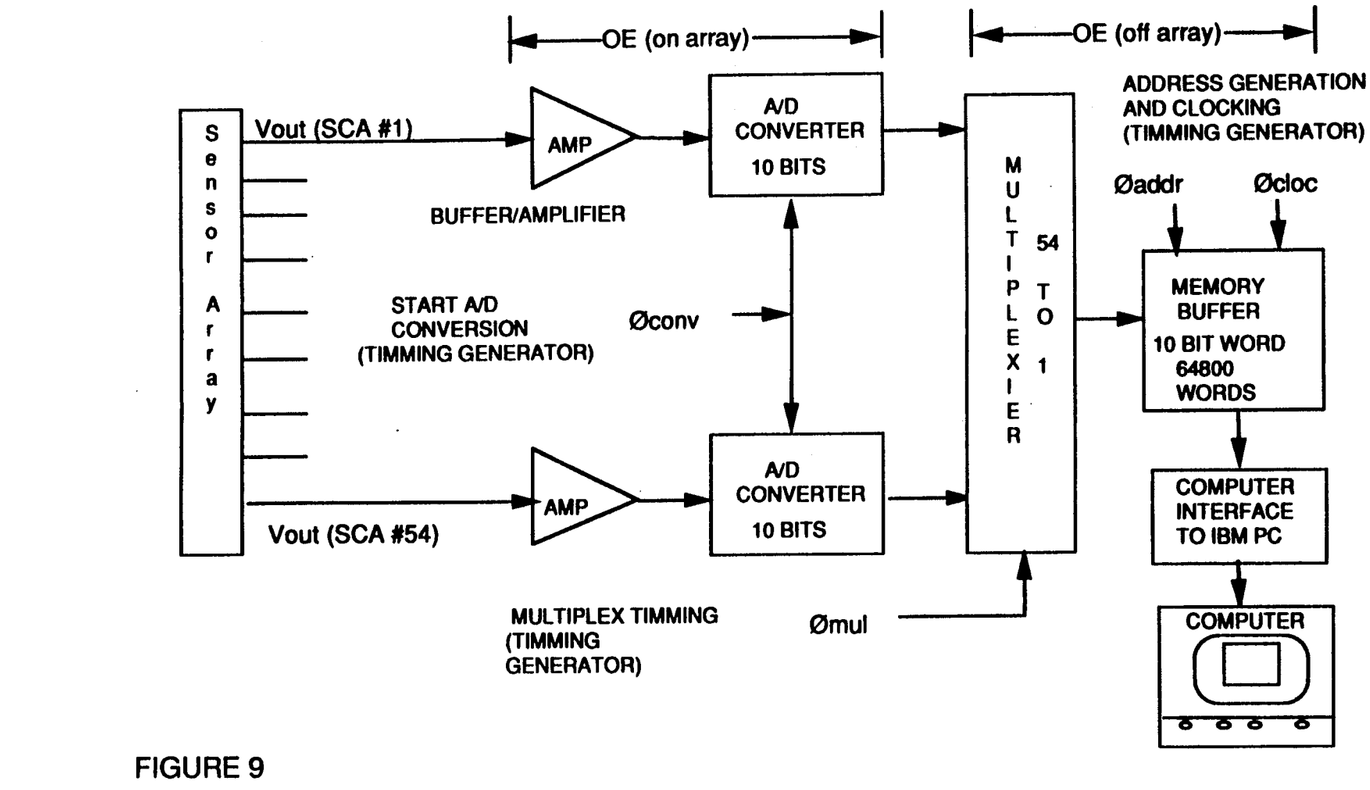
FIG. 9 is a schematic of the function of the output electronics of the present invention.

The OE, as depicted in FIG. 9, processes the data signals derived from each of the roughly 54 SCA'S. (Exact number of SCA'S depend upon imager and chip size). As shown in FIG. 9, part of the OE is located on the sensor array 6 (see FIG. 2) and part off the sensor array 3 (see FIG. 1). The first stage of the OE consist of a buffer/amplifier to enhance the SCA output drive capability and to correct for any non-uniformity in detector responsively. The output of the buffer stage will feed into a 10 bit A/D converter to give a dynamic range of about a 1000 to 1. Each of the A/Ds is multiplexed into a high speed buffer memory. This high speed memory is needed to interface to an augmented IBM-PC or other computer (not shown) for additional signal conditioning/processing for enhanced imaging and graphic display. A graphics terminal (25 FIG. 1) displays the image in real time and is able to archive images for storage and later use.

Figure 10:
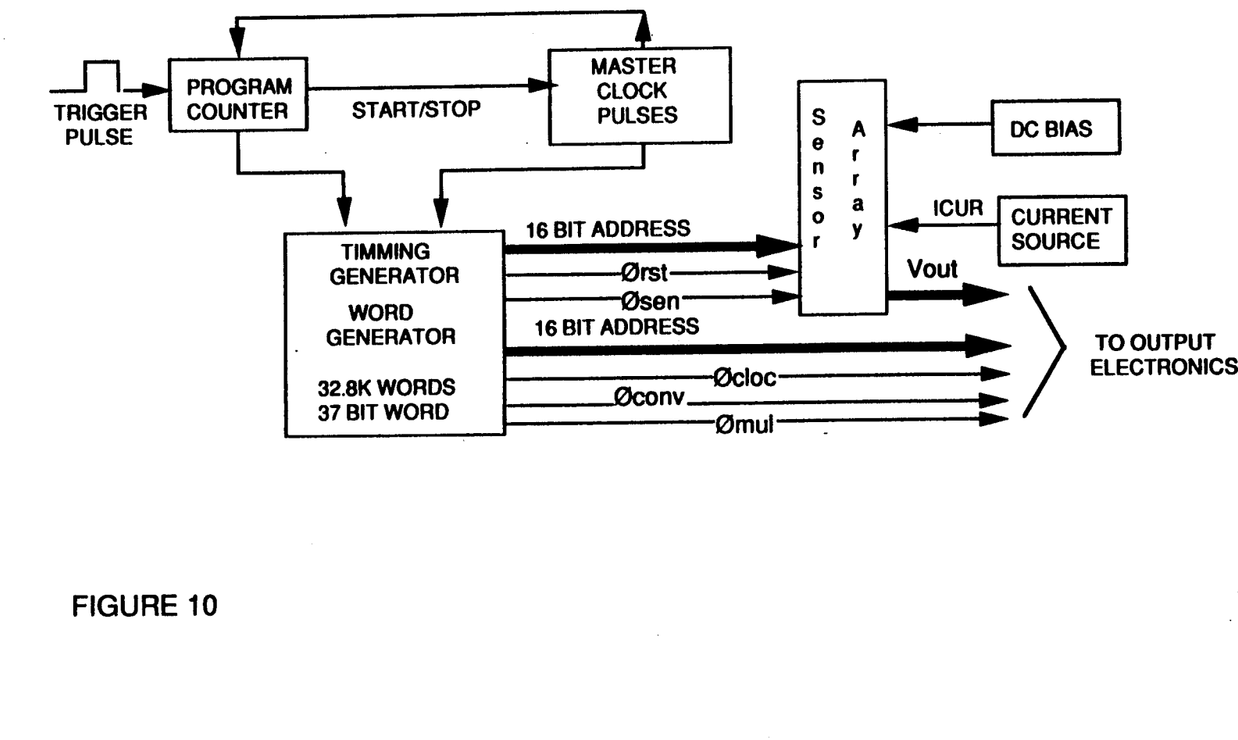
FIG. 10 is a schematic of the function of the drive electronics of the present invention.

The DE depicted in FIG. 10 serves to provide all of the necessary clocks and bias to drive each of the 54 SCAs and also provide some critical timing pulses for the OD unit. The DE is located off the sensor array 3 (see FIG. 1). The initiation of all DE start-up cycles/SCA data cycles is controlled by a trigger pulse from the x-ray source identifying a start of an exposure. This trigger pulse will start a program counter used in starting and stopping of all data cycles.

A data cycle is composed of two major sub-cycles. The first sub-cycle consist of collecting data while the x-ray source is exposed. The second cycle is used as background reference data and is subtracted from the first major cycle at the computer to enhance the image. The program counter is driven by a master clock that controls the speed of all sensor electronics. The timing generator consist of 32768 words with each word 37 bits long. Each bit of a word drives a clock line and each word is programmed to represent the desired pattern of that particular clock line. The speed at which each word is cycled through is controlled by the master clock. One complete pass through each data cycle is the same as cycling through all 32768 words. The program counter counts to 32768 and then issues a stop cycle pulse disabling the master clock. The current source and DC bias's is generated using discrete electronic components. All clocks and bias's generated by the DE feed either the sensor array 2 or the OD unit.

Although detailed embodiments of the present invention have been provided for both the high energy and diagnostic x-ray environment, the present invention is not limited to only those embodiments, but also includes uses and adaptations that would be equivalent to those defined in the following claims.

I claim:

1. A high resolution high-energy-x-ray digital imager for therapeutic x-rays comprising a sensor array and circuitry for timing and signal conditioning, said sensor array comprising a plurality of sensor chip arrays, associated converters, and output electronics chips, said sensor chip arrays each having associated therewith a plurality of detectors and readout electronics comprising signal storage capacitors separate from said detectors, said detectors and readout electronics adapted to change state in response to an x-ray pulse, producing data indicative of the change of state, said output electronics adapted to provide said data in digitized form in real time with data indicative of the location of said detector.

2. The high resolution high-energy-x-ray digital imager of claim 1 wherein the plurality of sensor chip arrays covers an area sufficient for radiological evaluation and is configured for continuous chip to chip detector coverage.

3. The high resolution high-energy-x-ray digital imager of claim 1 wherein the sensor chip array comprises a plurality of PIN detector and readout electronics unit cells and said circuitry comprises off-chip sensor processing electronics comprising drive electronics and said output electronics, said readout electronics being adapted to read out in real time stored data from said unit cells, and transfer it in digital form to a portion of said off-chip processing electronics.

4. The high resolution high-energy-x-ray digital imager of claim 3, said unit cell comprising a signal storage capacitor, wherein said capacitor is adapted to store a signal indicative of x-ray photon flux intensity.

5. The high resolution high-energy-x-ray digital imager of claim 4, said unit cell further comprising electronic means to reset said capacitor just before and after an x-ray pulse.

6. The high resolution high-energy-x-ray digital imager of claim 1 wherein a converter is located beneath each sensor chip array, said converter having at least the thickness of the x-ray attenuation length, wherein the converter enhances the x-ray detection efficiency of each sensor ship and shields the chip from tissue generated Compton electrons.

7. The high resolution high-energy-x-ray digital imager of claim 1 wherein said readout electronics is direct readout electronics adapted to read out said data in digitized form and in real time.

8. The high resolution high-energy-x-ray digital imager of claim 1 wherein said sensor chip arrays comprise switch means to isolate said detectors from said associated readout electronics, said switch means adapted to switch into a readout circuit when said x-ray pulse is on and out of the readout circuit when said x-ray pulse is off.

9. The high resolution high-energy-x-ray digital imager of claim 1, wherein said readout electronics is positioned on said chip array and comprises amplifier and digitizer means, wherein said detector signals are adapted to be driven off the array for further processing.

10. The high resolution high-energy-x-ray digital imager of claim 1 wherein said sensor array is mounted on an x-ray shielding support structure.

11. A multi-layered sensor, said sensor comprising a layer of high density metal at least the thickness of the x-ray attenuation length and a sensor chip array, said sensor chip array comprising a plurality of unit cells comprising PIN detectors and associated readout electronics comprising signal storage capacitors separate from said detectors, said PIN detectors and associated readout electronics adapted to change state in response to an x-ray pulse, and to produce data indicative of the change of state.

12. The multi-layered sensor of claim 11, wherein said signal storage capacitor is adapted to store a signal indicative of the intensity of x-ray photon flux.

13. The multi-layered sensor of claim 12, said unit cell further comprising electronic means to reset said capacitor just before and after an x-ray pulse.

14. A high resolution diagnostic x-ray digital imager comprising a sensor array and circuitry for timing and signal conditioning, said sensor array comprising a plurality of sensor chip arrays, an associated scintillator, and output electronics chips, said sensor chip arrays each comprising a plurality of PIN detectors and associated readout electronics comprising signal storage capacitors separate from said detectors, said detectors and associated readout electronics adapted to change state in response to an x-ray pulse, producing data indicative of the change of state, said electronics adapted to read out said data in digitized form in real time with data indicative of the location of said detector.

15. The high resolution diagnostic x-ray digital imager of claim 14 wherein the plurality of sensor chip arrays covers an area sufficient for radiological evaluation and is configured for continuous chip to chip detector coverage.

16. The high resolution diagnostic x-ray digital imager of claim 14 wherein the sensor chip array comprises a plurality of PIN detector and readout electronics unit cells and said circuitry comprises off-chip sensor processing electronics, said readout electronics being adapted to read out in real time stored data from said unit cells, and transfer it in digital form to a portion of said off-chip processing electronics.

17. The high resolution diagnostic x-ray digital imager of claim 16, wherein said signal storage capacitor is adapted to store a signal indicative of x-ray photon flux intensity.

18. The high resolution diagnostic x-ray digital imager of claim 17, said unit cell further comprising electronic means to reset said capacitor just before and after an x-ray pulse.

19. The high resolution diagnostic digital imager of claim 14 wherein scintillator material is beneath each sensor chip array, said scintillator material having about the thickness of the x-ray attenuation length, adapted to enhance the x-ray detection efficiency of each sensor chip.

20. The high resolution diagnostic x-ray digital imager of claim 14 wherein said sensor chip arrays comprise switch means to isolate said detectors from said associated readout electronics, said switch means adapted to switch into a readout circuit when said x-ray pulse is on and out of the readout circuit when said x-ray pulse is off.

21. The high resolution diagnostic x-ray digital imager of claim 14 wherein said readout electronics is positioned on said chip array and comprises amplifier and digitizer means, wherein said detector signals are adapted to be driven off the array for further processing.

22. The high resolution diagnostic x-ray digital imager of claim 14 wherein said sensor array is mounted on an x-ray shielding support structure.

23. A multi-layered sensor, said sensor comprising a first layer of scintillator material about the thickness of the x-ray attenuation length and one or more additional layers each comprising a sensor chip array, said sensor chip array comprising a plurality of unit cells, each unit cell comprising detectors and readout electronics adapted to change state in response to an x-ray pulse, producing data indicative of the change of state, said readout electronics comprising signal storage capacitors separate from said detectors.

24. The multi-layered sensor of claim 23, wherein said signal storage capacitor is adapted to store a signal indicative of the intensity of x-ray photon flux.

25. The multi-layered sensor of claim 24, said unit cell further comprising electronic means to reset said capacitor just before and after an x-ray pulse.

* * * * *